US006508834B1

(12) United States Patent
Pinchasik et al.

(10) Patent No.: US 6,508,834 B1
(45) Date of Patent: *Jan. 21, 2003

(54) ARTICULATED STENT

(75) Inventors: Gregory Pinchasik, Ramat Hasharon (IL); Jacob Richter, Ramat Hasharon (IL)

(73) Assignee: Medinol Ltd., Ramat Hasharon (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/483,082

(22) Filed: Jan. 14, 2000

Related U.S. Application Data

(63) Continuation of application No. 09/026,750, filed on Feb. 20, 1998, now Pat. No. 6,059,811, which is a continuation of application No. 08/760,359, filed on Dec. 4, 1996, now Pat. No. 5,980,552, which is a continuation of application No. 08/455,462, filed on May 31, 1995, now abandoned, which is a continuation of application No. 08/213,272, filed on Mar. 17, 1994, now Pat. No. 5,449,373.

(51) Int. Cl.[7] .................................................. A61F 2/06
(52) U.S. Cl. ........................................................ 623/1.16
(58) Field of Search ............................ 606/1, 108, 194, 606/195, 158, 198; 621/1.1, 1.11, 1.16, 12; 623/1.15, 1.16, 1.17, 1.18

(56) References Cited

U.S. PATENT DOCUMENTS

| 4,733,665 A | 3/1988 | Palmaz |
| 4,762,128 A | 8/1988 | Rosenbluth |
| 4,800,882 A | 1/1989 | Gianturco |

(List continued on next page.)

FOREIGN PATENT DOCUMENTS

| EP | 0 335 341 | 4/1989 |
| EP | 0 540 290 | 5/1993 |
| EP | 0 541 443 | 5/1993 |
| EP | 0 566 807 | 10/1993 |
| EP | 0 606 165 | 7/1994 |
| WO | WO 95/31945 | 11/1995 |
| WO | WO 96/03092 | 2/1996 |

Primary Examiner—David H. Willse
Assistant Examiner—Suzette J. Jackson
(74) Attorney, Agent, or Firm—Kenyon & Kenyon

(57) ABSTRACT

An articulated stent for delivering through a bodily conduit, for example, a peripheral or coronary artery, which has one or more curved portions and for implantation therein. The articulated stent includes at least two substantially rigid segments and a flexible connector for connecting adjacent segments. The connector assumes a cylindrical configuration when relaxed and a differentially stretched and compressed curved configuration when flexed.

14 Claims, 5 Drawing Sheets

U.S. PATENT DOCUMENTS

| | | |
|---|---|---|
| 4,830,003 A | 5/1989 | Wolff et al. |
| 4,856,516 A | 8/1989 | Hillstead |
| 4,886,062 A | 12/1989 | Wiktor |
| 4,922,905 A | 5/1990 | Strecker |
| 4,950,227 A | 8/1990 | Savin et al. |
| 4,969,458 A | 11/1990 | Wiktor |
| 4,994,071 A | 2/1991 | MacGregor |
| 5,019,085 A | 5/1991 | Hillstead |
| 5,019,090 A | 5/1991 | Pinchuk |
| 5,035,706 A | 7/1991 | Giantureo |
| 5,102,417 A | 4/1992 | Palmaz |
| 5,104,404 A | 4/1992 | Wolff |
| 5,116,365 A | 5/1992 | Hillstead |
| 5,133,732 A | 7/1992 | Wiktor |
| 5,158,548 A | 10/1992 | MacGregor |
| 5,161,547 A | 11/1992 | Tower |
| 5,195,984 A | 3/1993 | Schatz |
| 5,282,824 A | 2/1994 | Gianturco |
| 5,314,472 A | 5/1994 | Fontaine |
| 5,330,500 A | 7/1994 | Song |
| 5,354,308 A | 10/1994 | Simon et al. |
| 5,354,309 A | 10/1994 | Schepp et al. |
| 5,383,892 A | 1/1995 | Cardon et al. |
| 5,405,377 A | 4/1995 | Cragg |
| 5,441,515 A | 8/1995 | Khosravi et al. |
| 5,443,496 A | 8/1995 | Schwartz et al. |
| 5,449,373 A * | 9/1995 | Pinchasik et al. .......... 623/1.16 |
| 5,507,767 A | 4/1996 | Maeda et al. |
| 5,540,712 A | 7/1996 | Kleshinski et al. |
| 5,554,181 A | 9/1996 | Das |
| 5,643,312 A | 7/1997 | Fischell et al. |
| 5,649,952 A | 7/1997 | Lam |
| 5,651,174 A | 7/1997 | Schwartz et al. |
| 5,653,727 A | 8/1997 | Wiktor |
| 5,980,552 A * | 11/1999 | Pinchasik et al. .......... 623/1.16 |
| 6,059,811 A * | 5/2000 | Pinchasik et al. .......... 623/1.16 |
| 6,348,065 B1 * | 2/2002 | Brown et al. ............... 623/1.16 |

\* cited by examiner

ARTICULATED STENT

RELATED PATENT APPLICATIONS

This application is a continuation of prior application Ser. No. 09/026,750 filed Feb. 20, 1998, (now U.S. Pat. No. 6,059,811) which is a continuation of Ser. No. 08/760,359 filed Dec. 4, 1996 (now U.S. Pat. No. 5,980,552), which is a continuation of Ser. No. 08/455,462 filed May 31, 1995 (abandoned), which is a continuation of Ser. No. 08/213,272 filed Mar. 17, 1994 (now U.S. Pat. No. 5,449,373).

FIELD AND BACKGROUND OF THE INVENTION

The present invention relates to stents which are implanted as part of a balloon angioplasty procedure within a bodily conduit of a living animal or a human to maintain patency. In particular, the present invention relates to articulated intravascular stents for delivery through or implantation in a blood vessel having a curved portion.

Intravascular stents having a constricted diameter for delivery through a blood vessel and an expanded diameter for applying a radially outwardly extending force for supporting the blood vessel are known in the art. Articulated intravascular stents for either delivery through a curved blood vessel or implanted therein are also known in the art.

Self-expandable articulated stents are described, for example, in U.S. Pat. No. 5,104,404 entitled "Articulated Stent" to Wolff. Balloon expandable articulated stents are commercially available under the trade name Palmaz-Schatz Balloon-Expandable Stents from Johnson & Johnson Intervention Systems Co.

A prior art self-expandable articulated intravascular stent 10 deployed in a curved blood vessel 16 is now described with reference to FIG. 1 which is, in actual fact, FIG. 2 of the above referenced U.S. Pat. No. 5,104,404. Stent 10 is made up of a number of individual segments 12 articulated by hinges 14 connected at each end to segments 12. Stent 10 is preferably fabricated from memory shape material, for example, nitinol, and as such is self expandable after delivery from a delivery system described in U.S. Pat. No. 4,830,003 to Wolff et al. However, these prior art articulated intravascular stents suffer from a number of disadvantages both during delivery through a curved blood vessel and when implanted therein as will now described.

The delivery of stent 10 through curved blood vessel 16 is more complicated than the delivery of a non-articulated stent in that stent 10 has to be angularly oriented such that its hinges 14 are located towards the convex portion of blood vessel 16 so that stent 10 can be flexed inward. In the present example, it will be noted that hinges 14 are located on the same side of segments 12 because blood vessel 16 has only a simple curve in one plane. It can be readily appreciated that delivery of stents through blood vessels which have one or more curved portions which are not in the same plane is even more complicated and generally requires specially constructed stents.

Even when implanted in a curved blood vessel 16, stents 10 are shown to be lacking in that the gaps between segments 12 render the curved portion of blood vessel 16 without support. Furthermore, the gaps at the convex portion of blood vessel 16 are substantially greater than the gaps at the concave portion thereof, thereby inducing non-uniform and therefore undesirable stresses on blood vessel 16.

Therefore, it would be highly desirable to have an articulated stent which does not require any particular angular orientation when being delivered through a curved bodily conduit and provides continuous and uniform support for both straight and curved portions of a bodily conduit when implanted.

It would also be highly desirable the structure of a stent does not depend on the particular orientations of curved portions of a blood vessel.

SUMMARY OF THE INVENTION

The object of the present invention is for an articulated stent which can be delivered through a curved bodily conduit using a routine medical procedure and a conventional stent delivery system. Furthermore, the stent provides continuous and uniform support for both straight and curved portions of a bodily conduit when implanted. Still further, the structure of a stent and its support of a bodily conduit do not depend on the orientations of the curved portions of the conduit.

The objective of the present invention is achieved by an articulated stent, comprising: (a) at least two substantially rigid segments; and (b) a flexible connector for connecting adjacent segments, wherein the connector assumes a substantially cylindrical configuration when relaxed and a differentially stretched and compressed curved configuration when flexed.

After expansion, the rigid segments of the stent preferably present a fine diamond shaped mesh having 1 mm long sides to provide continuous and uniform support for straight portions of a bodily conduit.

The connectors can be implemented as a plurality of substantially helical links connecting adjacent segments. Alternatively, the connectors can be implemented as links each having at least one kink. The connectors typically have between 8–24 links to provide continuous and uniform support for both straight and curved portions of a bodily conduit.

The stents have constricted diameters for intraluminal delivery and are then deformed, by the inflation of a balloon forming part of their catheter delivery system, to expanded diameters for applying radially outwardly extending forces for supporting the lumen of bodily conduits. The constricted and expanded diameters of the stents typically fall in the ranges of 1.0–3.5 mm and 3.5–10.0 mm, respectively.

The stents are preferably fabricated from low memory, more plastic than elastic, bio-compatible materials, for example, stainless steel 316L, gold, tantalum, etc. which enables them to be plastically deformed from their constricted diameters to their expanded diameters.

A typical stent for implantation in a human coronary artery is 9–21 mm long comprising three to seven 2.2 mm long stent segments connected by two to six 1 mm long connectors such that the ends of the stent subtend between a 45° to 135° angle at a radius of curvature of approximately 9 mm when flexed.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of an articulated stent for delivering through a curved bodily conduit, for example, a peripheral or coronary artery of a living animal or a human and implantation therein as part of a balloon angioplasty procedure to maintain patency.

The principles and operation of the articulated stent of the present invention may be better understood with reference to the drawings and the accompanying description.

Figure 1:
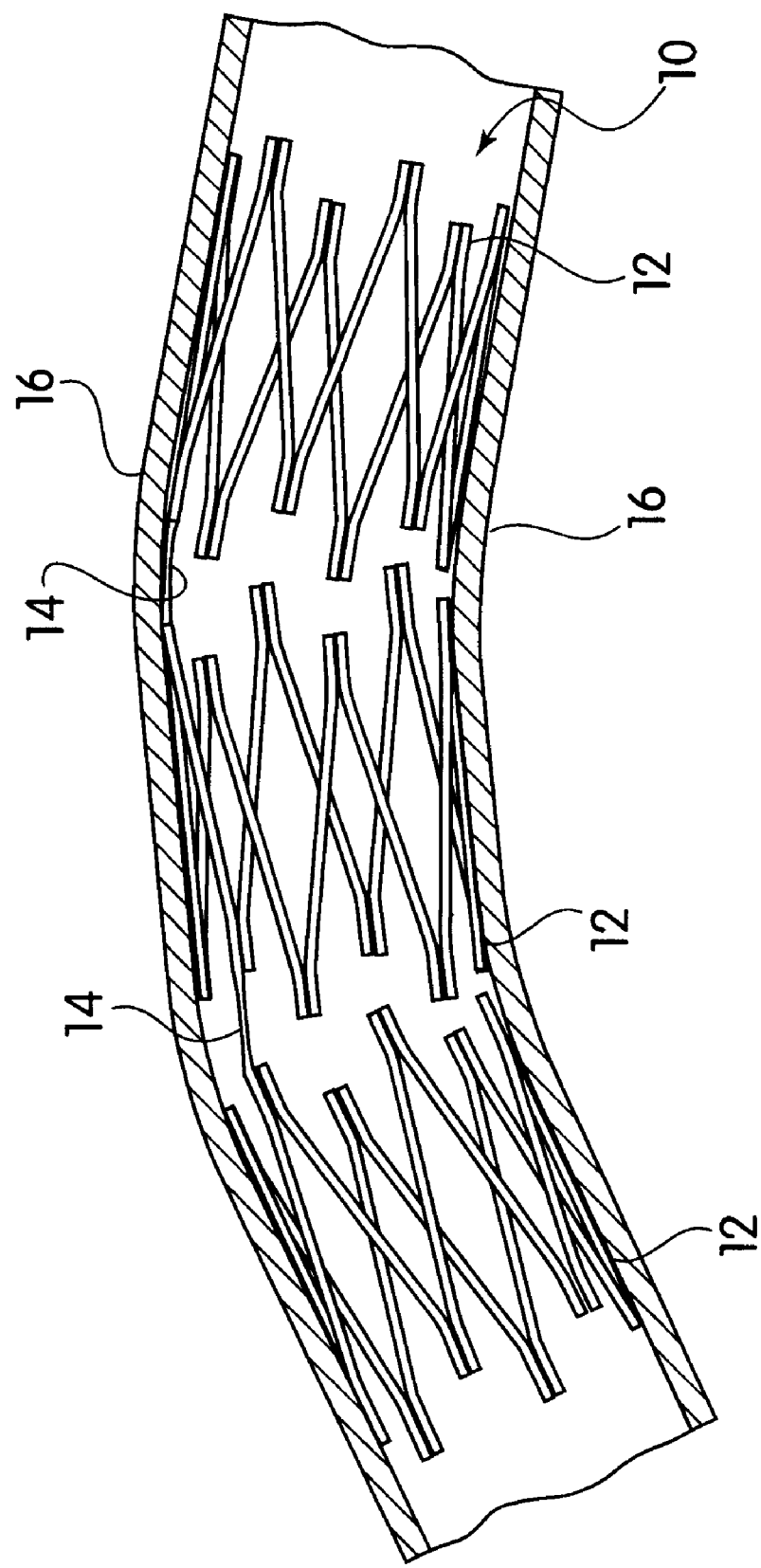
FIG. 1 shows a close-up view of a prior art articulated stent of deployed in a curved blood vessel.
Figure 2A:
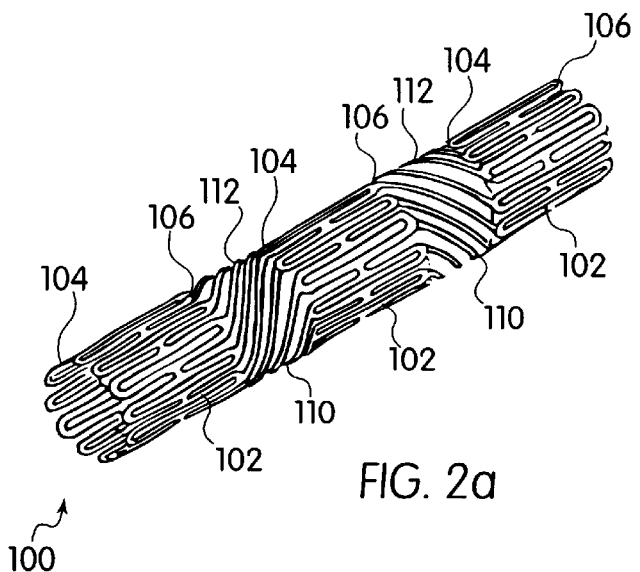
FIGS. 2a and 2b show a preferred embodiment of an articulated stent, constructed and operative according to the teachings of the present invention, in its relaxed and flexed states before plastic deformation.
Figure 2B:
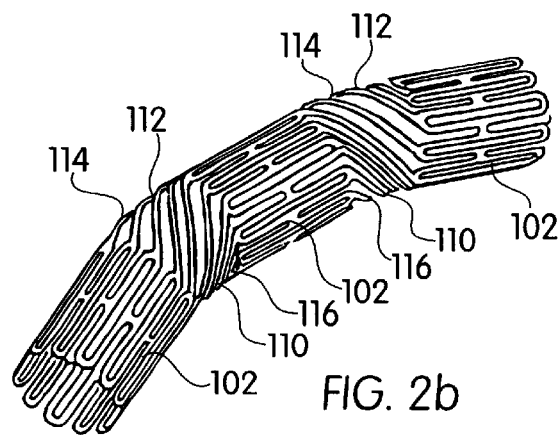
Figure 2C:
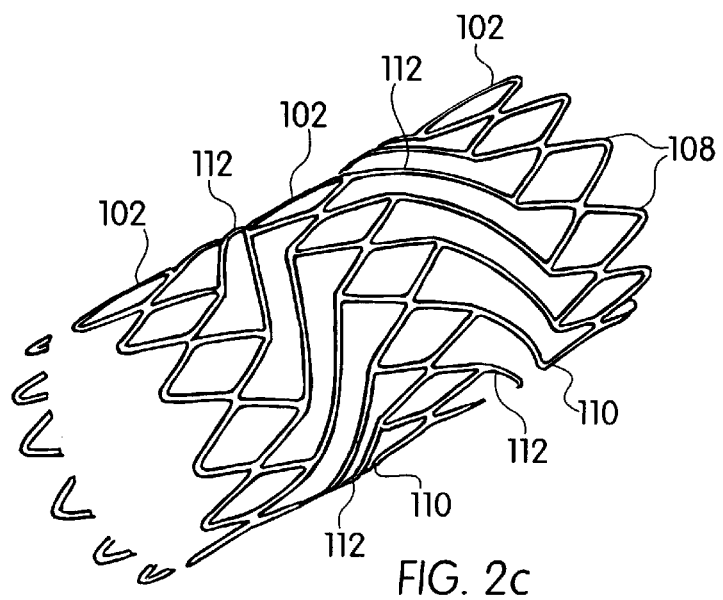
FIG. 2c shows the expanded stent of FIG. 2 after plastic deformation.

Referring now to the drawings, FIGS. 2a–2c show an articulated stent, generally designated 100, constructed and operative according to the teachings of the present invention, generally comprising a number of substantially rigid segments 102 connected by connectors 110.

Segments 102 are preferably made up to present a fine diamond mesh of interconnected diamond shaped cells 108 having 1 mm sides on expansion as best seen in FIG. 2c. Depending on the intended diameter of stent 100, segments 102 typically comprise between 8–24 diamond shaped cells 108.

Connectors 110 comprise links 112 connecting a front end 104 to a tail end 106 of adjacent segments 102. Links 112 preferably extend in a substantially helical fashion between apexes of diamond shaped cells 108 at front and rear ends 104 and 106 of adjacent segments 102 such that the number of links 112 equals the number of cells 108. Links 112 are preferably evenly deployed around perimeters of segments 102 such that connectors 110 can be equally flexed in any direction and to provide continuous and uniform support to both straight and curved portions of a bodily conduit.

Alternate connectors 110 at front and rear ends 104 and 106, respectively, of a segment 102 preferably have links 112 wound in clockwise and counter clockwise directions. Alternately winding connectors 110 ensures that the rotational displacement of links 112 and adjacent segments 102 relative to the walls of a blood vessel and more importantly the balloon of its delivery system is minimized when stent 100 is expanded.

It is particular feature of the present invention that connectors 110 have a generally cylindrical configuration when stent 100 is relaxed as best seen in FIG. 2a and a differentially stretched and compressed curved configuration when stent 100 is flexed as best seen in FIG. 2b. The flexed configuration is brought about by two relatively opposing displacements of links 112. First, the differential stretching of connectors 110 occurs at the convex portion thereof denoted 114 by links 112 being displaced away from one another. Second, the differential compressing of connectors 110 occurs at the concave portion thereof denoted 116 by links 112 being displaced towards one another.

Stent 100 has a constricted diameter for delivery through a curved bodily conduit as shown in FIGS. 2a and 2b and an expanded diameter as shown in FIG. 2c for supporting a bodily conduit. Stent 100 is preferably fabricated from low memory, more plastic than elastic, bio-compatible material, for example, stainless steel 316L, gold, tantalum, etc. which enables it to be plastically deformed from its constricted diameter to its expanded diameter. The constricted and expanded diameters of stent 100 typically fall in the ranges of 1.0–3.5 mm and 3.5–10.0 mm, respectively.

Figure 2D:
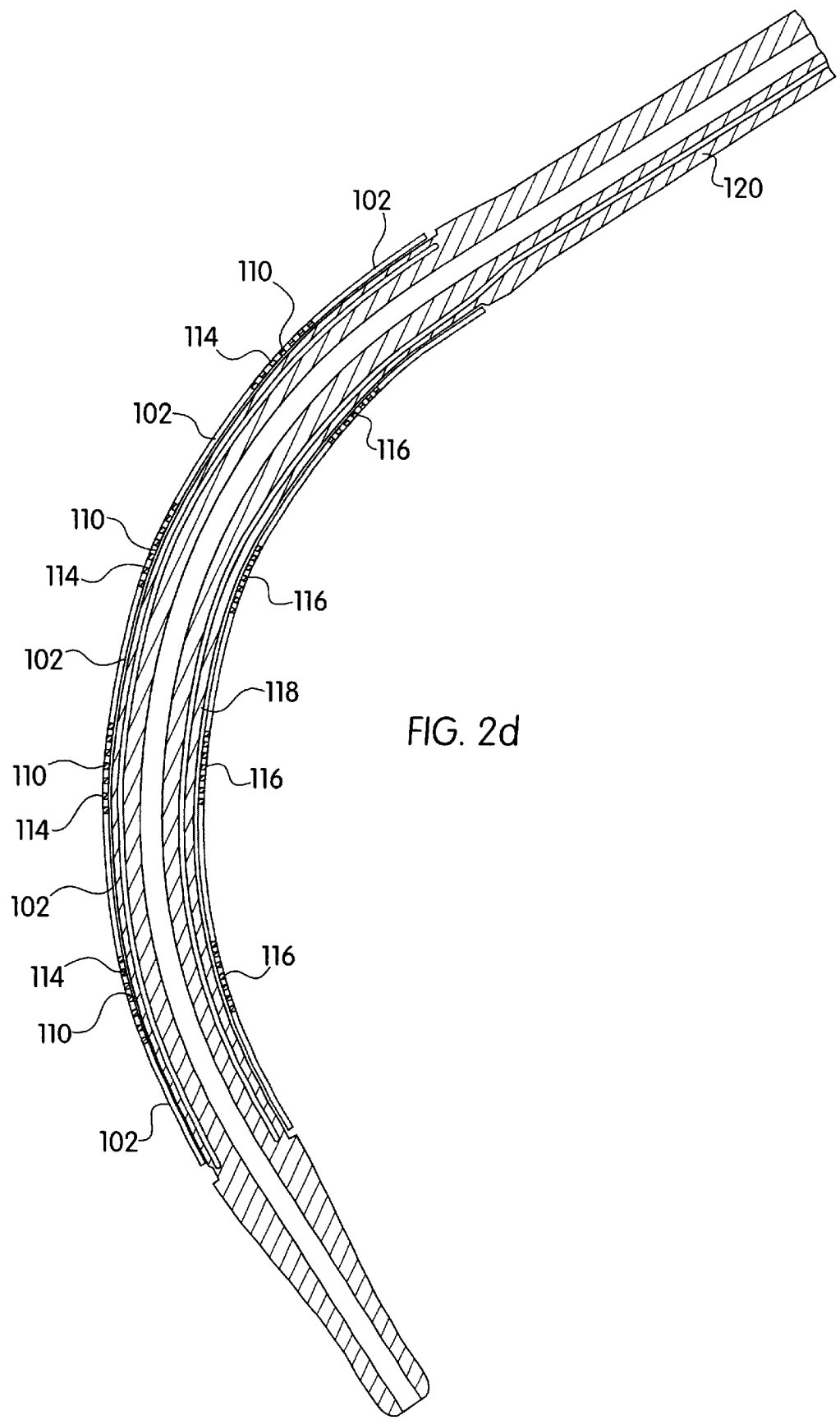
FIG. 2d shows the stent of FIG. 2 mounted on a catheter in its flexed state.
Figure 2E:
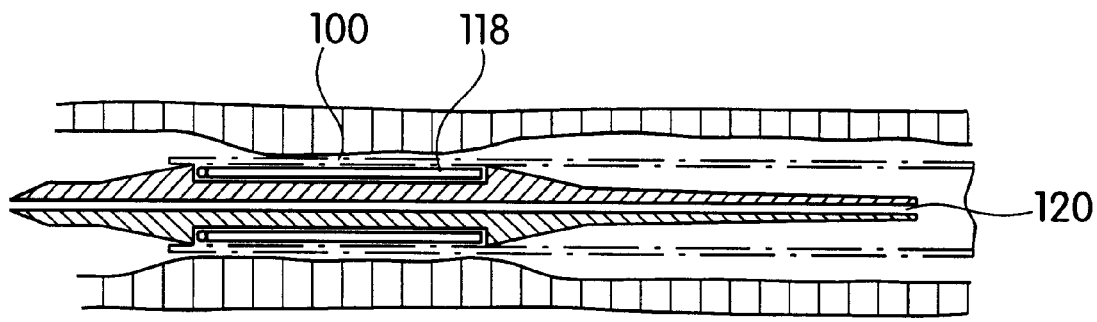
FIGS. 2e and 2f show the stent of FIG. 2 before and after expansion by a balloon forming part of its catheter delivery system.
Figure 2F:
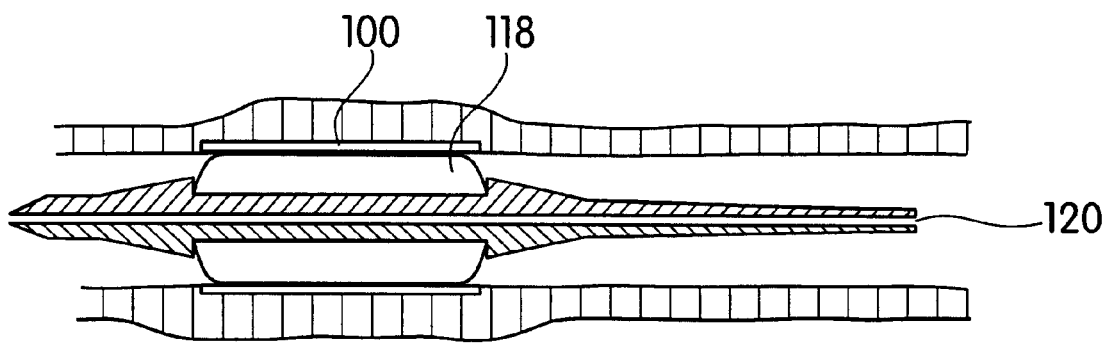

With reference now to FIGS. 2d–2f, stent 100 is shown overlying a balloon 118 forming part of its catheter delivery system 120. Stent 100 is mounted on its catheter delivery system 120 in its constricted diameter state shown in FIG. 2e for plastic deformation through inflation of balloon 118 to its expanded diameter shown in FIG. 2f for supporting the walls of a bodily conduit. An exemplary stent for implantation in a human coronary artery, is typically 15 mm long made up of five 2.2 mm long segments 102 connected by four 1 mm long connectors 110 and capable of flexion such that its ends subtend a 90° angle at a radius of curvature of approximately 9 mm.

The delivery of articulated stent 100 is considerably simpler than the delivery of prior art articulated stent 10 because stent 100 is equally flexible in all direction and therefore does not require a dedicated angular orientation to pass a particular curved portion. This advantage is particularly important for delivery through blood vessels having multiple curved portions. It is a further advantage of stent 100 over prior art stents 10, that stent 100 provides continuous and uniform support along the entire length of a blood vessel by means of segments 102 and unflexed connectors 110 supporting straight portions thereof while connector portions 114 and 116 supporting convex and concave curved portions thereof, respectively.

Figure 3A:
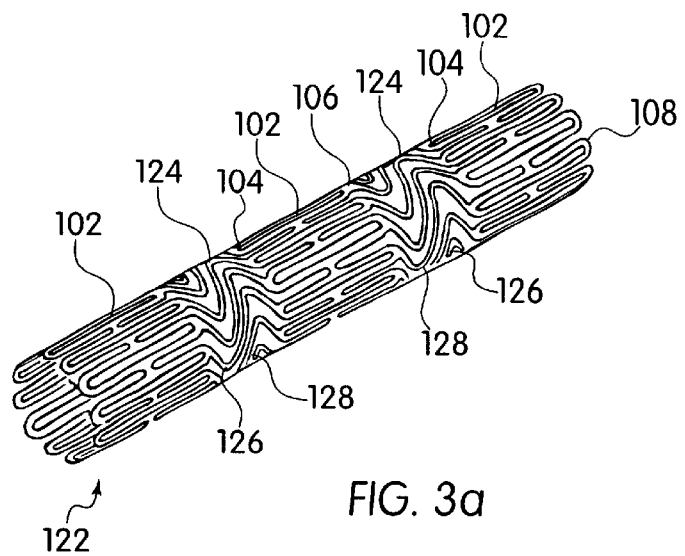
FIGS. 3a and 3b show a second embodiment of an articulated stent, constructed and operative according to the teachings of the present invention, in its relaxed and flexed states before plastic deformation.
Figure 3B:
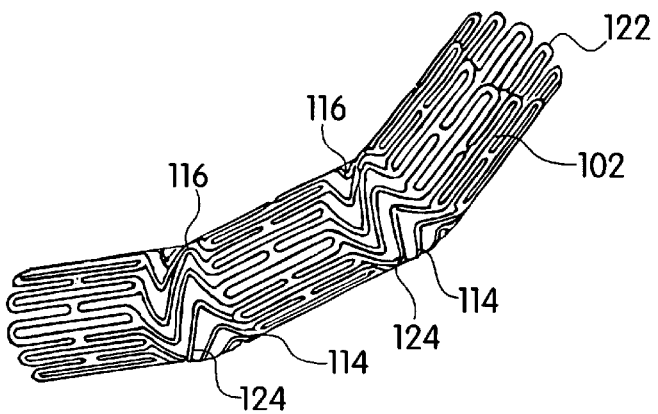

With reference now to FIGS. 3a and 3b, an articulated stent 122 is shown in which connectors 124 comprise links 126 having one or more kinks 128. The design of connectors 124 is preferred to that of connector 110 because stent 100 may have a tendency to rupture balloon 118 due to two reasons. First, links 112 overlying the convex portion of balloon 118 have a tendency to be biased inward when stent 100 is flexed. Second, segments 102 display a rotational displacement relative to balloon 118 when stent 100 is expanded.

In this case, the differentially stretched and compressed curved configuration of connector 124 is brought about by two relatively opposing displacements of links 112 as before except that the differential stretching of connectors 124 at convex portion 114 occurs by kinks 128 being somewhat straightened out while the differential compressing of connectors 124 at concave portion 116 occurs by kinks 128 being more acutely bent.

Figure 3C:
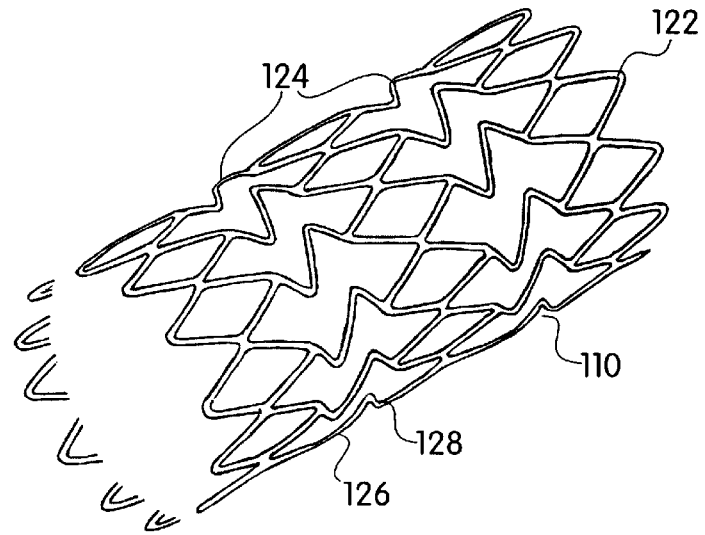
FIG. 3c shows the expanded stent of FIG. 3 after plastic deformation.

In a similar fashion to stent 100, stent 122 has a constricted diameter for delivery through a curved bodily conduit as shown in FIGS. 3a and 3b and an expanded diameter as shown in FIG. 3c for supporting a bodily conduit when implanted therein.

While the invention has been described with respect to a limited number of embodiments, it will be appreciated that many variations, modifications and other applications of the invention may be made.

What is claimed is:

1. An articulated stent, comprising:
    (a) at least two substantially rigid segments having, upon expansion, a plurality of connected cells each having apices, each of said rigid segments presenting a substantially cylindrical structure; and (b) a flexible connector, comprising a plurality of flexible links, disposed between the substantially rigid segments, each of the links connecting apices of adjacent cells on adjacent rigid segments, each of the links, when viewed laterally, having at least a first portion and a second portion and an area of inflection disposed between the first portion and the second portion.

2. The articulated stent of claim 1, wherein the area of inflection remains inflected after the expansion of the stent.

3. The articulated stent of claim 1, wherein the first portion and second portion are of different lengths and wherein the length of the larger of the portions is not greater than twice the length of the shorter of the portions.

4. The articulated stent of claim 1, wherein the area of inflection enlarges during the expansion of the stent.

5. The articulated stent of claim 1, wherein the first portion and second portion are substantially straight.

6. The articulated stent of claim 5, wherein the first portion and second portion are of different lengths and wherein the length of the larger of the portions is not greater than twice the length of the shorter of the portions.

7. The articulated stent of claim 6, wherein said substantially rigid segments are substantially rigid particularly when compared to said flexible connectors disposed between the substantially rigid segments.

8. The articulated stent of claim 6, wherein the area of inflection remains inflected after the expansion of the stent.

9. The articulated stent of claim 6, wherein the area of inflection enlarges during the expansion of the stent.

10. The articulated stent of claim 5, wherein the area of inflection remains inflected after the expansion of the stent.

11. The articulated stent of claim 5, wherein said substantially rigid segments are substantially rigid particularly when compared to said flexible connectors disposed between the substantially rigid segments.

12. The articulated stent of claim 5, wherein the area of inflection enlarges during the expansion of the stent.

13. The articulated stent of claim 1, wherein the substantially cylindrical structure comprises a mesh.

14. The articulated stent of claim 1, wherein said substantially rigid segments are substantially rigid particularly when compared to said flexible connectors disposed between the substantially rigid segments.

* * * * *